United States Patent [19]
Dickinson et al.

[11] Patent Number: 4,477,346
[45] Date of Patent: Oct. 16, 1984

[54] METHOD FOR THE REMOVAL OF INTERFERING SUBSTANCES IN THEOPHYLLINE ASSAYS

[75] Inventors: Johanne C. Dickinson; William A. Frey, both of Wilmington, Del.

[73] Assignee: E. I. Du Pont de Nemours and Company, Wilmington, Del.

[21] Appl. No.: 487,896

[22] Filed: Apr. 22, 1983

Related U.S. Application Data

[62] Division of Ser. No. 334,165, Dec. 24, 1981, Pat. No. 4,460,695.

[51] Int. Cl.³ .............................................. B01D 15/00
[52] U.S. Cl. ................................. 210/198.2; 210/656; 210/636; 422/70
[58] Field of Search ...................... 210/635, 656, 198.2; 55/67, 386; 524/379; 422/70

[56] References Cited

U.S. PATENT DOCUMENTS

| | | | |
|---|---|---|---|
| 3,966,596 | 6/1976 | Stevens et al. | 210/198.2 |
| 4,243,534 | 1/1981 | Bulbenko | 210/198.2 |
| 4,338,404 | 7/1982 | Tanaka et al. | 210/635 |
| 4,353,801 | 10/1982 | Mukoyama et al. | 210/635 |

OTHER PUBLICATIONS

Chromatographic and Allied Methods by Mikes, John Wiley & Sons of New York, pp. 221-225, 1979.

*Primary Examiner*—John Adee
*Attorney, Agent, or Firm*—George A. Frank

[57] ABSTRACT

An apparatus for the separation of theophylline and caffeine contained in body fluids is provided. A macroreticular styrene-divinylbenzene copolymer resin activated by a protic solvent is utilized. The body fluid is eluted with water in an isocratic manner to afford a theophylline sample uncontaminated with caffeine. Such samples are useful in immunoassay procedures for the measurement of theophylline.

6 Claims, No Drawings

METHOD FOR THE REMOVAL OF INTERFERING SUBSTANCES IN THEOPHYLLINE ASSAYS

This is a divisional of application Ser. No. 334,165 filed Dec. 24, 1981 now U.S. Pat. No. 4,460,695.

TECHNICAL FIELD

This invention relates to a novel method of separating caffeine from theophylline in a biological sample to allow the substantially interference-free measurement of theophylline.

BACKGROUND ART

Theophylline (1,3-dimethylxanthine) is a commonly use drug in the treatment of bronchial asthma in adults and children. Assays for theophylline are important because patients show a variable response to standard dosage regimens and because there is a relatively small dosage range between sub-therapeutic and toxic doses.

Caffeine (1,3,7-trimethylxanthine) is a commonly encountered exogenous substance in human blood. It is structurally similar to theophylline except for the presence of the 7-methyl group. Anitibodies raised to theophylline are often unable to distinguish between caffeine and theophylline and hence may react with both. This phenomenon of cross-reactivity is undesirable in an assay for theophylline since it may result in values higher than actual. Therefore, in an immunoassay for theophylline, the removal of caffeine interference is necessary.

At present, the most commonly employed immunological assays for theophylline depend on antibody specificity to reduce caffeine interference. The need to produce specific antibodies is a disadvantage, however, since the necessary specific immunogens are often difficult or expensive to synthesize and since reproducible, specific antibodies are difficult to elicit from animals.

Another method for measuring theophylline and caffeine utilizes liquid chromatography. A variety of separation methods and column materials is known in the art. These suffer from several disadvantages for routine clinical assays since they require specialized, expensive equipment and have to employ organic solvents which are not compatible either with the biological samples or with assay systems. This incompatibility requires a separate extraction step to free the theophylline and caffeine from the serum sample.

The literature abounds with references to the adsorption of organic species by high surface area hydrophobic styrene-divinylbenzene copolymers and the wetting of their surfaces by organic solvents prior to use; see, for example, U.S. Pat. No. 3,531,463, issued Sept. 29, 1970 and Pranitis, et al., Journal of Forensic Sciences, Volume 19, 917 (1974).

The subsequent elution of the adsorbed species is also commonplace. Separation of the adsorbed species, however, usually has to be accomplished by subsequent chromatographic techniques, often involving step wise or gradient elution rather than isocratic elution and often requiring organic solvents.

An Application Note by E. I. du Pont de Nemours and Company for the PREP TM I Automated Sample Processor discloses a two-step method for measuring quantities of theophylline in human serum and plasma. The first step is an extraction of the lipophilic components, including theophylline and caffeine, utilizing a styrene-divinylbenzene copolymer resin. The second step is reverse phase high pressure liquid chromatography during which the separation of caffeine and the photometric measurement of theopylline occur. Both of these steps require organic solvents.

There is a need for a simple column technique for reducing caffeine interference in a theophylline immunoassay by an aqueous, isocratic elution of theophylline without the concomitant elution of caffeine.

DISCLOSURE OF THE INVENTION

This invention involves a method for producing a substantially completely caffeine-free biological sample from body fluid containing at least theophylline and caffeine and comprises the steps of
 (A) introducing body fluid onto a column containing water-insoluble, hydrophobic, macrorecticular resin having a particle size range of 40–500 $\mu$m and a surface area range of 300–400 $m^2/g$ and which has been preactivated with protic solvent; and
 (B) eluting by isocratic aqueous elution the biological sample containing at least 90% of the theophylline and less than 15% of the caffeine originally in the serum.

This invention further involves a method for measuring theophylline content of a biological sample comprising the steps of
 (A) introducing body fluid onto a column containing water-insoluble, hydrophobic, macrorecticular resin having a particle size range of 40–500 $\mu$m and a surface area range of 300–400 $m^2/g$ and which has been preactivated with protic solvent;
 (B) eluting by isocratic aqueous elution the biological sample containing at least 90% of the theophylline and less than 15% of the caffeine originally in the body fluid; and
 (C) measuring theophylline content in an immunoassay.

A filled column capable of producing a substantially completely caffeine-free biological sample suitable for the measurement of its theophylline content is also contemplated. This column consists essentially of a packing which is
 (A) water-insoluble, hydrophobic, macrorecticular resin having a particle size range of 40–500 $\mu$m and a surface area range of 300–400 $m^2/g$, slurried in
 (B) protic solvent.

DESCRIPTION OF THE INVENTION

The method of this invention is useful in removing substantially completely caffeine interference in immunoassays for theophylline. Biological samples obtained by this method contain caffeine levels which permit the performance of clinically significant theophylline immunoassays. The method utilizes a column which provides for the elution of theophylline while substantially retaining caffeine.

The column packing material utilized in the method of this invention is a water-insoluble, macroreticular polymeric adsorbent. A preferred material is a styrene-divinylbenzene copolymer characterized by high surface area, preferably 300–400 $m^2/g$, broad pore-size distribution, and high porosity. One such material is "Amberlite" XAD-2, available from the Rohm and Hass Company. Amberlite XAD-2 is 2% crosslinked and has an effective size of 400 $\mu$m with a surface area of 300 $m^2/g$ and is useful for the adsorption of water soluble organic substances.

Some styrene-divinylbenzene copolymers can be made more active in the method of this invention by grinding them into smaller size, larger surface area particles. These particles can be classified into particles having a mean particle diameter of approximately 60 μm. Such material has an increased surface area of approximatley 350 m²/g thereby leading to more efficient adsorption of water soluble organic substances. Ground paticles can also be utilized in admixture with unground polymeric adsorbent.

The column can optionally also contain a second resin such as styrene-divinylbenzene copolymer with similar particle size but greatly reduced sruface area. This second resin is substantially inert as an adsorbent for the purpose of this invention and serves as a filler material. The second resin reduces the adsorption efficiency of the first resin in a given volume and allows more convenient column sizes and eluent quantities. Having two resins of similar particle size, homogeneous, stable and reproducible columns can be prepared. A preferred material useful as the second, optional resin is a styrene-divinylbenzene copolymer, "Bio-Beads" S-X12, available from Bio-Rad Laboratories. This resin is 12% crosslinked and has a mean particle diameter of approximately 60 μm with a surface area of approximately 0.2 m²/g.

It was found unexpectedly that the column system of this invention, when preactivated with protic solvents such as n-butanol, n-propanol, isopropanol, methanol, etc., substantially completely retains caffeine while eluting theophylline during an aqueous, isocratic elution. Less than 15%, preferably less than 10%, of the caffeine in a biological sample containing 5 to 50 μg/mL caffeine is eluted through the column. Thus, the eluate from this column contains theophylline substantially free of caffeine and is suitable for the measrement of theophylline in an immunoassay procedure.

Preactivation of the column materials with protic solvents such as isopropanol is necessary for the method of this invention. The column materials can be slurried with isopropanol or aqueous isopropanol prior to packing the columns. Pure isopropanol or aqueous mixtures containing at least 15% isopropanol are useful in preactivating the column material. A preferred mode is to use a volume of 25% (v/v) isopropanol in water equal to the weight of the resin.

The method of this invention is carried out by injecting a sample containing theophylline and caffeine onto the column and eluting isocratically with aqueous solvents until greater than 90% of the theophylline in the sample is eluted. A recovery of greater than 90% of the theophylline can be obtained over the clinically useful range of 5 to 40 μg/mL theophylline in human samples. The samples can be body fluids such as blood plasma or blood serum.

By isocratic elution is meant a chromatographic elution with one solvent of constant composition as opposed to a gradient or stepwise elution with solvents of varying compositions.

By aqueous elution is meant an elution using deionized water or deionized water containing various inorganic salts or buffers. As a practical matter, the eluate can contain a small quantity of isopropanol, preferably less than 5% by volume.

While the exact mechanism of the separation of caffeine and theophylline is not understood, it is believed that this method is a liquid-liquid extraction between the mobile water phase and the stationary isopropanol phase, with the extraction situs at the large surface area of the first resin.

The recovery of theophylline and retention of caffeine are dependent upon the quantity of the activated, classified particles of the first resin in the column and the volume of aqueous solvent used in the elution process. At constant elution rate and elution volume, increased quantities of active particles in the column will decrease theophylline recovery but increase the caffeine retention while lower ratios of active to inactive particles in the column will increase the theophylline recovery but decrease the caffeine retention. Thus it is possible to prepare columns which allow substantially complete recovery of theophylline from the sample while substantially completely removing caffeine interference. Greater than 90% recovery of theophylline and less than 15% elution of caffeine, within prescribed sample concentration ranges of theophylline and caffeine, are considered clinically acceptable for biological samples to be analyzed. A convenient method of finding the optimum conditions for a given column size, elution rate and elution volume is to analyze the eluates from columns containing various ratios of active to inactive particles for both caffeine and theophylline content. A useful technique for doing this is high pressure reverse phase liquid chromatography as described in the PREP TM I Application Note referred to above.

There are several known immunoassay procedures for the measurement of theophylline. These include radioimmunoassays, enzyme modulated immunoassays, fluorescence immunoassays, and particle enhanced turbidimetric inhibition immunoassays. The method of this invention has been found to be particularly useful in connection with the particle enhanced turbidimetric inhibition immunoassay as described in our copending application Ser. No. 315,922, filed Oct. 28, 1981 by A. R. Craig, et al. In such an assay a human serum sample containing 10 μg/mL theophylline and 10 μg/mL caffeine was found to give an error of 75% in the measurement of theophylline when the serum sample was not treated with the column of this invention and only a 7% error when the column was used. An additional advantage of this invention is that other interfering serum components can be simultaneously adsorbed and retained on the column.

EXAMPLE

A. Preparation of Column

A styrene-divinylbenzene copolymer resin, "Amberlite" XAD-2, Type W, with a mean diameter of 200 to 500 μm (nominal mesh size of 20 to 50), is ground in an Alpine Pinmill, Model 160Z (Alpine American Corporation, Natick, Mass.) at a rotor speed of 11,200 rpm and a feed rate of 1 lb. (454 g) per minute and sized in a boundary layer air classifier to the 40 to 100 μm range. After processing, the resin has a surface area of approximately 350 m²/g and a mean particle diameter of 60 μm.

A second styrene-divinylbenzene copolymer resin, "Bio-Beads" S-X12, is dry blended with XAD-2 in a ratio of 16 parts S-X12 to 1 part XAD-2. The S-X12 resin has a surface area of approximately 0.2 m²/g and a mean particle diameter of 60 μm.

The above resin blend is then slurried with a volume of 25% isopropanol/water equal to the resin weight. After thorough mixing, the slurry is packed into columns.

A column useful in the method of this invention is designed for use in automated separations on an automatic clinical analyzer (available from E. I. du Pont de Nemours and Company as the 'aca'). The 'aca ' column is a plastic tube approximately 5.5 mm in diameter and 88 mm long with rubber stoppers at both ends which allow for automatic sample and diluent entry and eluate exit into an analytical test pack. Such an analytical test pack is described in U.S. Pat. No. Re 29,725, issued Aug. 8, 1978 to D. R. Johnson, et al. which is hereby incorporated by reference.

The 'aca' column is packed with approximately 1 g of the XAD-2/S-X12 resin slurry and contains approximately 59 mg of XAD-2. The column is continuous, noncompressible and free from voids. The column is maintained in the 25% isopropanol/water mixture and is not allowed to dry.

B. Separation of Caffeine from Samples Containing Theophylline

The 'aca' column prepared in step A above is inserted into an 'aca' analytical test pack for the automated separation of caffeine from the sample. In the first step, a 0.020-ml human serum sample containing unknown quantities of caffeine and theophylline is injected onto the column. Deionized water (4.0 mL) is then pumped through the column at a rate of 0.068 mL/second. Greater than 90% of the theophylline in the original serum sample is eluted through the column while less than 10% of the caffeine passes through. After this step, the 'aca' analytical test pack contains a 4.0mL aqueous solution of theophylline substantially free of caffeine.

C. Measurement of Theophylline

Theophylline is measured in a particle enhanced turbidimetric inhibition immunoassay as disclosed in application Ser. No. 315,922.

The assay is performed at 37° C. on an 'aca' instrument. To the test pack containing a 4.0-mL aqueous solution of theophylline as described in step B above is added 1.0 mL of buffer containing 0.750 M Potassium phosphate, 0.125 M glycine and 0.5% Gafac RE-160 (an anionic surfactant available from GAF. Corp.), pH 9.52. After approximately one minute, 0.036 mL of rabbit anti-theophylline antiserum (Kallestad Laboratories, Inc.), which has previously been diluted 1 part antiserum to 4 parts buffer containing 0.150 M phosphate, pH 7.8, is added together with two tablets containing sufficient polyethylene glycol (PEG) 8000 to give a final concentration of PEG in the reaction mixture of 2.5% (w/v). After a 3.5-minute incubation period, the turbidimetric reaction is initiated with the addition of 0.050 mL of the particle reagent prepared as described in Example 12 of Ser. No. 315,922. The particle reagent is made up of theophylline-human serum albumin conjugates covalently attached to latex particles having a polystyrene core and polyglycidyl methacrylate shell. The increase in turbidity due to particle aggregation is measured as the difference in absorbance at 340 nm (rate of change) 29 s and 46 s after particle addition. Table 1 shows the data for a standard curve for the assay of theophylline; the results obtained with the unknown sample are compared to this curve to provide the amount of theophylline present. (Theophylline standards are prepared by appropriately diluting with human serum a solution of known concentration of theophylline in water. Caffeine can be added in a similar fashion. The assay results from these standards provide the data for the standard curve.)

TABLE 1

Inhibition of Turbidimetric Activity by Serum Theophylline

| Theophylline Concentration ($\mu$g/mL) | Rate (mA/min at 340 nm) |
| --- | --- |
| 0 | 205 |
| 2.5 | 167 |
| 5.0 | 132 |
| 10.0 | 90 |
| 20.0 | 64 |
| 40.0 | 44 |

Comparative caffeine inteference in the measurement of a sample containing 10 $\mu$g/mL theophylline is carried out by utilizing identical analytical test packs with and without columns. In the noncolumn analytical test packs, 4.0 mL of water containing 3% isopropanol (to simulate the level of isopropanol eluted through the column) is added to 1.0 mL of the buffer and 0.020 mL of human serum sample. The two types of analytical test packs are then processed identically. The data in Table 2 show considerable reduction in caffeine interference when the sample is treated by the column method of this invention.

TABLE 2

Effect of Column in Reducing Caffeine Interference in Theophylline Assays

| Pack with Column | | Pack without Column | |
| --- | --- | --- | --- |
| Caffeine Concentration ($\mu$g/mL) | % Error | Caffeine Concentration ($\mu$g/mL) | % Error |
| 10 | 7% | 10 | 75% |
| 25 | 20% | 25 | 160% |
| 50 | 55% | 50 | 233% |

We claim:

1. A filled column cpable of producing a substantially completely caffeine-free biological sample suitable for the measurement of its theophylline content by liquid-liquid extraction consisting essentially of a packing which is
    (A) water-insoluble, hydrophobic, macrorecticular resin having a particle size range of 40-500 $\mu$m and a surface area range of 300-400 m$^2$/g, slurried in
    (B) protic solvent.

2. The column of claim 1 wherein the packing also contains a second resin having a particle size similar to the particle size of the first resin but a surface area less than the surface area of the first resin.

3. The column of claim 1 wherein the protic solvent is isopropanol.

4. The column of claim 1 wherein said resin is a styrene-divinylbenzene copolymer and has a particle size range of 40-100 $\mu$m and a surface area of approximately 350 m$^2$/g.

5. The column of claim 4 wherein said resin has a mean particle diameter of 60 $\mu$m.

6. The column of claim 1 wherein said resin has a mean particle diameter of 60 $\mu$m and wherein the column also contains a second resin of similar particle size and a surface area of approximately 0.2 m$^2$/g.

* * * * *